United States Patent
Robinson

(10) Patent No.: US 6,569,175 B1
(45) Date of Patent: May 27, 2003

(54) SURGICAL KNIFE

(75) Inventor: Christopher Robinson, Lawrenceville, NJ (US)

(73) Assignee: Alcon, Inc., Hunenberg (CH)

(*) Notice: Subject to any disclaimer, the term of this patent is extended or adjusted under 35 U.S.C. 154(b) by 0 days.

(21) Appl. No.: 09/992,388

(22) Filed: Nov. 14, 2001

(51) Int. Cl.$^7$ .................................................. A61F 9/00
(52) U.S. Cl. ......................... 606/166; 30/286; 606/167
(58) Field of Search .............................. 606/166, 167, 606/181, 182; 30/61, 526, 162, 286, 151, 335

(56) References Cited

U.S. PATENT DOCUMENTS

| | | |
|---|---|---|
| 2,390,309 A | 12/1945 | Keys |
| 4,576,164 A | 3/1986 | Richeson |
| 4,735,202 A | 4/1988 | Williams |
| 5,254,128 A | 10/1993 | Mesa |
| 5,417,704 A * | 5/1995 | Wonderley ................. 606/167 |

* cited by examiner

Primary Examiner—David O. Reip
Assistant Examiner—D. Jacob Davis
(74) Attorney, Agent, or Firm—Jeffrey S. Schira

(57) ABSTRACT

A knife having a handle into which a knife blade may be inserted. The blade end of the handle is of reduced diameter and contains a pair of spring-like cantilevered locking arms. The locking arms terminate in a clasping mechanism that interact with a latch contained within a bore in a sheath. The bore is sized and shaped to reciprocate linearly over the blade end of the handle so as to alternatively cover the blade for storage or expose the blade for use.

8 Claims, 3 Drawing Sheets a
SURGICAL KNIFE

BACKGROUND OF THE INVENTION

This invention relates generally to the field of surgical knives and, more particularly, to ophthalmic surgical knives.

A variety of surgical knives may be used during ophthalmic surgery to make or modify the opening incision into the globe. These knives are generally made from stainless steel or diamond. While steel knives can be used more than once, most steel knives are intended to be a single use disposable product. Diamond knives are designed to be a reusable item because diamond knives are expensive relative to steel knives.

There has been increasing interest in developing a reusable or limited reusable steel knife. One of the problems of developing such a knife is the damage that the unprotected knife blade might receive when being resterilizing between uses. Various knife guards are available, but have proven to be unsatisfactory.

For example, U.S. Pat. No. 5,254,128 discloses a knife with an extendable sleeve that may be alternatively moved to protect the blade or retracted to expose the blade for use. The locking mechanism for this sleeve is disclosed as being either a screw thread or a spring-loaded ball that locks within a groove. This patent also mentions the use of a bowed leaf spring attached at both ends with a projection that snaps into a groove. The screw thread embodiment of this invention requires the use of two hands to operate and restricts cleaning and sterilization procedures. The spring-loaded ball is expensive and complicate to manufacture, and the bowed spring does not allow for independent adjustment of opening and closing force.

Accordingly, a need continues to exist for a surgical knife having a retractable blade guard that is simple and inexpensive to manufacture and that can be operated with only one hand.

BRIEF SUMMARY OF THE INVENTION

The present invention improves upon the prior art by providing a knife having a handle into which a knife blade may be inserted. The blade end of the handle is of reduced diameter and contains a pair of spring-like cantilevered locking arms. The locking arms terminate in a clasping mechanism that interact with a latch contained within a bore in a sheath. The bore is sized and shaped to reciprocate linearly over the blade end of the handle so as to alternatively cover the blade for storage or expose the blade for use.

Accordingly, one objective of the present invention is to provide a knife having a handle with a pair of spring-like cantilevered locking arms.

Another objective of the present invention is to provide a knife having a reciprocating sheath that alternatively covers the blade for storage or exposes the blade for use.

These and other advantages and objectives of the present invention will become apparent from the detailed description and claims that follow.

DETAILED DESCRIPTION OF THE INVENTION

Figure 1:
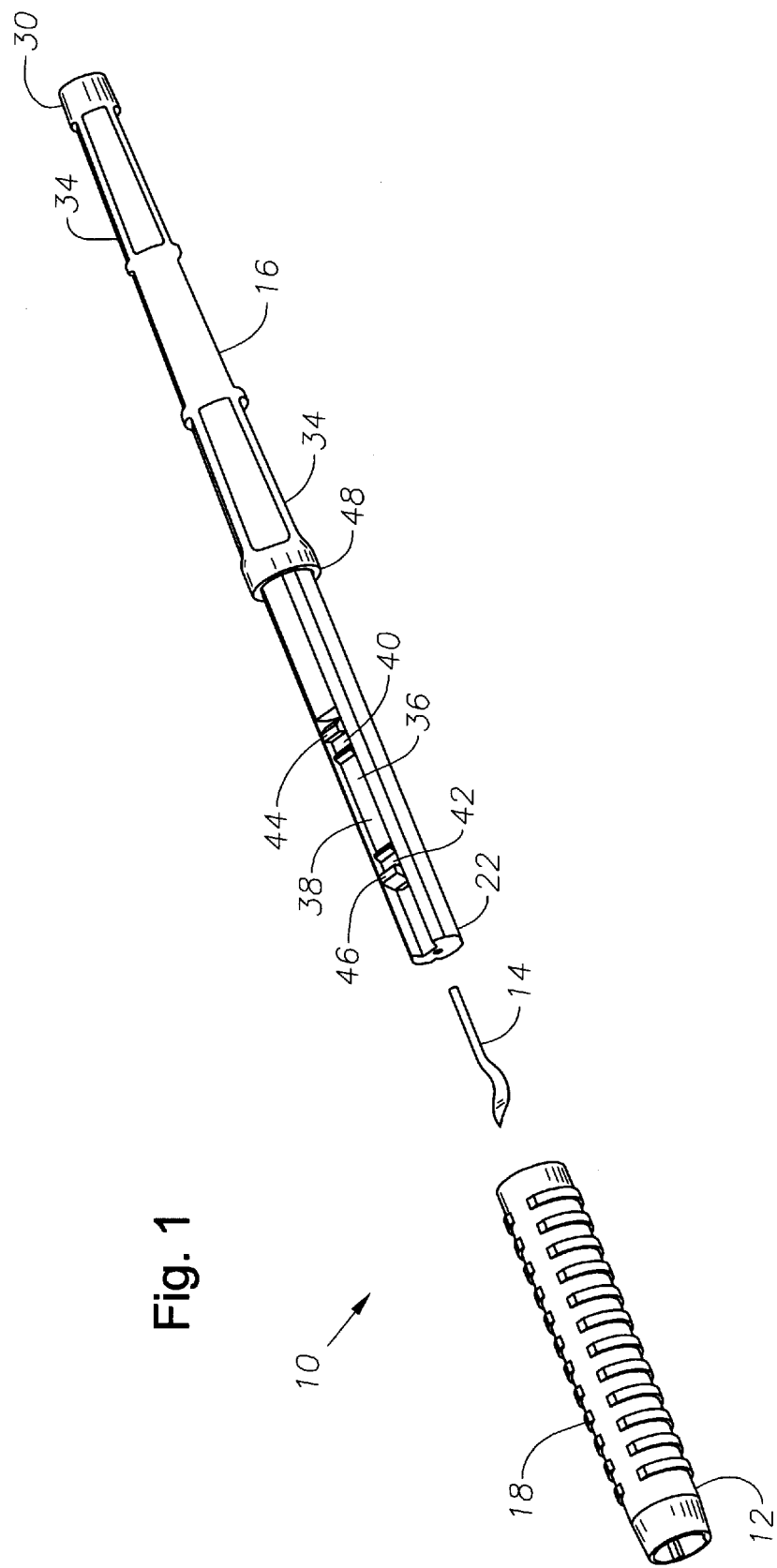
FIG. 1 is an exploded perspective view of the surgical knife of the present invention.
Figure 2:
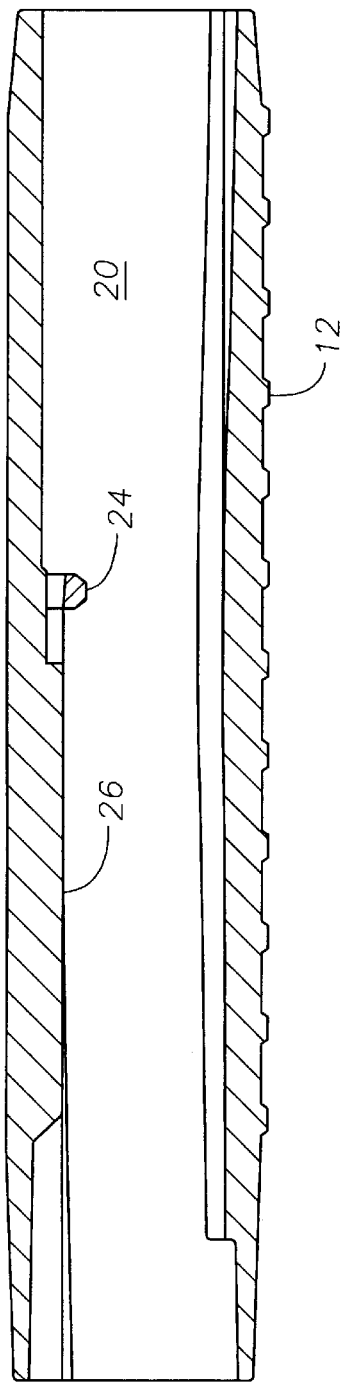
FIG. 2 is a cross-sectional view of the sheath used with the surgical knife of the present invention.

As seen in FIG. 1, knife 10 of the present invention generally includes sheath 12, blade 14 and handle 16. Blade 14 may be any suitable surgical blade made, for example, from stainless steel, titanium, diamond or diamond-coated substrate, such blades being well-known in the art. Sheath 12 and handle 14 preferably are made from injection-molded thermoplastic, but may also be made from other plastics, stainless-steel or titanium. Sheath 12 preferably contains ribs or knurling 18 to make sheath 12 easier to grip. Sheath 12 is tube-like and defines bore 20 that is sized and shaped to reciprocate linearly over blade end 22 of handle 16. As best seen in FIG. 2, projecting into bore 20 from sheath 12 is spring latch 24 and ramp 26. Latch 24 and ramp 26 interact with clasp 28 on blade end 22 of handle 16 in the manner discussed below.

Figure 3:
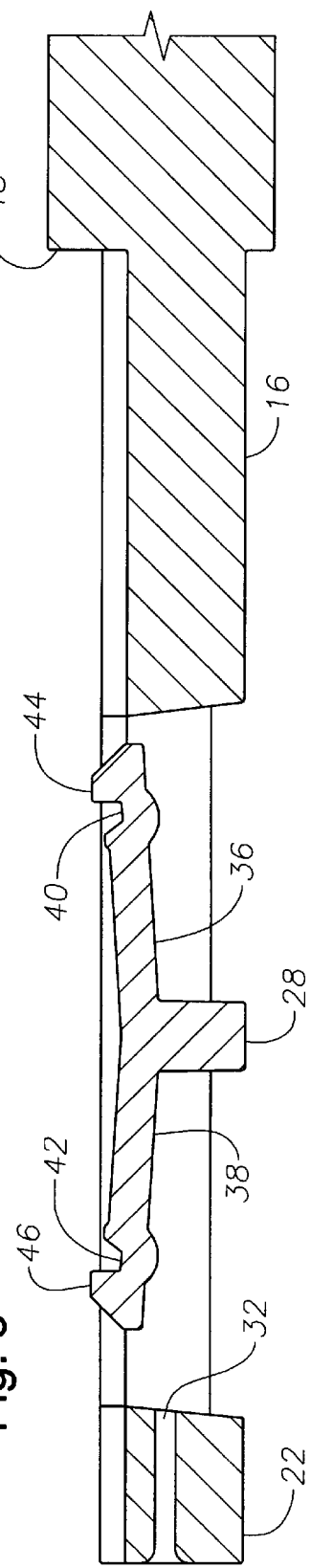
FIG. 3 is a cross-sectional view of the blade end of the handle used with the surgical knife of the present invention.

Handle 16 preferably is rod-like having blade end 22 and gripping end 30 opposite blade end 22. Gripping end 30 may contain a plurality of ridges 34 to allow handle 16 to be gripped more easily. As best seen in FIG. 3, blade end 22 is of slightly reduced diameter relative to gripping end 30 and contains bore 32 that is sized and shaped to receive blade 14. The diameter of blade end 22 is sized so that blade end 22 will linearly reciprocate within bore 20 of sheath 12. Projecting outwardly from blade end 22 of handle 16 are spring-like cantilevered locking arms 36 and 38 of clasp 28. Locking arms 36 and 38 contain detents 40 and 42, and locking pins 44 and 46, respectively.

Figure 4:
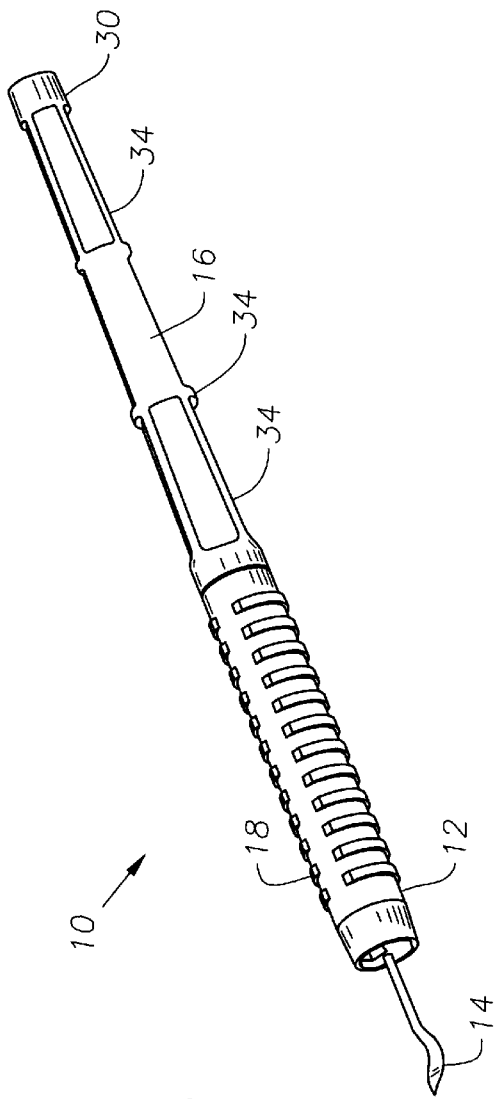
FIG. 4 is a perspective view of the surgical knife of the present invention showing the sheath retracted, exposing the blade.
Figure 5:
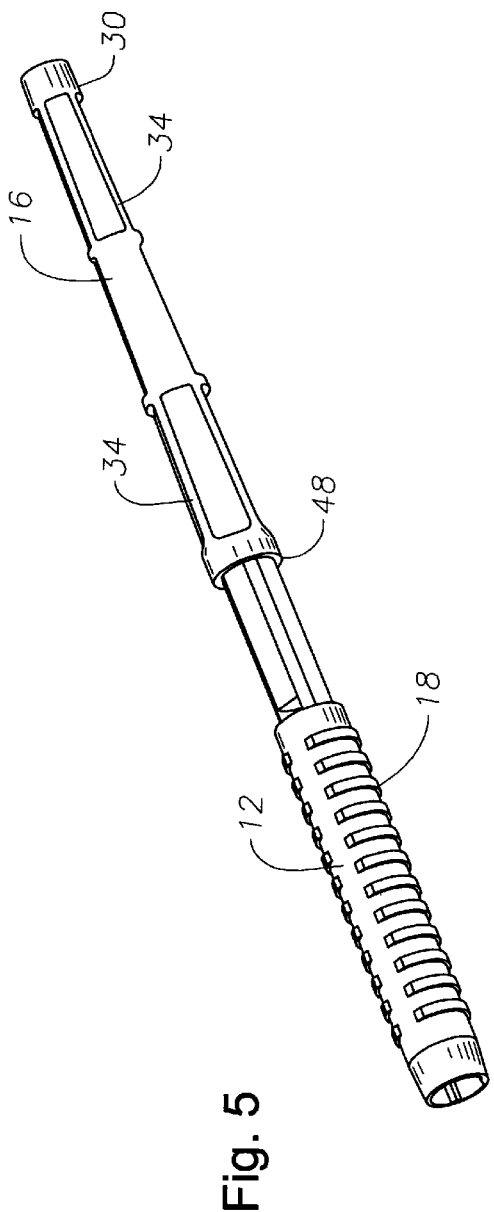
FIG. 5 is a perspective view of the surgical knife of the present invention showing the sheath extended, covering the blade.

In use, blade 14 is mounted within bore 32 of blade end 22 of handle 16 and fix by any suitable method, such as an adhesive. Sheath 12 is slid or threaded over blade end 22 of handle 16 until latch 24 contacts locking pin 46. Pushing sheath 12 with additional force cause latch 24 to ride up and over pin 46 and into detent 42 because of the spring-like construction of latch 24 and locking arm 38. With latch 24 held within detent 42, sheath 12 extends out and away from handle 16, thereby covering blade 14, as best seen in FIG. 5. Additional linear force on sheath 12 will cause latch 24 to ride up out of detent 42 and ride along locking arms 38 and 36 until latch 24 engages detent 40, thereby holding sheath 12 closer to gripping end 30 of handle 16 and exposing blade 14, as best seen in FIG. 4. Pin 44 and ridge 48 on handle 16 prevent additional rearward movement of sheath 12. With sheath 12 in the most rearward position shown in FIG. 4, locking arm 38 and locking pin 46 are compressed by ramp 26 in bore 20. Such compression firmly engages sheath 12 on handle 16 and helps prevent rocking or wobbling of sheath 12 on handle 16 with blade 14 is exposed, allowing knife 10 to be held by sheath 12 during use. Sheath 12 may be extended by pushing forwardly (away from gripping end 30 and toward blade end 22 of handle 16) on sheath 12, causing latch 24 to ride up and out of detent 40, along locking arms 38 and 36 and into detent 42.

An important aspect of the present invention is that the size and shape of locking arms 36 and 38 and detents 40 and 42 may be varied to provide for different locking forces and different forces when extending or retracting sheath 12. For example, detent 42 may be deeper and locking arm 38 may provide for more force so that sheath 12 is not easily accidentally retracted, exposing blade 14.

This description is given for purposes of illustration and explanation. It will be apparent to those skilled in the relevant art that changes and modifications may be made to the invention described above without departing from its scope or spirit.

We claim:

1. A surgical knife, comprising:
   a) a handle having a gripping end and a blade end, the blade end having a clasp comprising a pair of locking arms having detents;
   b) a blade associated with the blade end of the handle;
   c) a tubular sheath having a bore sized and shaped so as to allow the sheath to reciprocate linearly along the blade end of the handle; and
   d) a latch projecting from the sheath into the bore so that the latch engages the clasp when the sheath is reciprocated linearly along the blade end of the handle.

2. The surgical knife of claim 1 wherein the locking arms further contain locking pins.

3. The surgical knife of claim 2 wherein the sheath further comprises a ramp projecting into the bore so that at least one of the locking pins engages the ramp when the sheath is reciprocated linearly along the blade end of the handle.

4. The surgical knife of claim 1 wherein the locking arms vary in size.

5. The surgical knife of claim 1 wherein the detents vary in size.

6. A surgical knife, comprising:
   a) a handle having a gripping end and a blade end;
   b) a clasp associated with the blade end of the handle, the clasp having a pair of locking arms, each of the locking arms containing a detent and a locking pin;
   c) a blade associated with the blade end of the handle;
   d) a tubular sheath having a bore sized and shaped so as to allow the sheath to reciprocate linearly along the blade end of the handle;
   e) a latch projecting from the sheath into the bore so that the latch engages the locking arms and the detents when the sheath is reciprocated linearly along the blade end of the handle; and
   f) a ramp projecting from the sheath into the bore so that the latch engages at least one of the locking pins when the sheath is reciprocated linearly along the blade end of the handle.

7. The surgical knife of claim 6 wherein the locking arms vary in size.

8. The surgical knife of claim 6 wherein the detents vary in size.

* * * * *